US010791919B2

(12) United States Patent
Fujii

(10) Patent No.: US 10,791,919 B2
(45) Date of Patent: Oct. 6, 2020

(54) ENDOSCOPE SYSTEM AND ENDOSCOPE

(71) Applicant: OLYMPUS CORPORATION, Tokyo (JP)

(72) Inventor: Toshiyuki Fujii, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 323 days.

(21) Appl. No.: 15/953,555

(22) Filed: Apr. 16, 2018

(65) Prior Publication Data

US 2018/0228357 A1    Aug. 16, 2018

Related U.S. Application Data

(63) Continuation of application No. PCT/JP2017/019358, filed on May 24, 2017.

(30) Foreign Application Priority Data

Jun. 7, 2016    (JP) ................................. 2016-113496

(51) Int. Cl.
| *A61B 1/00* | (2006.01) |
| *A61B 1/12* | (2006.01) |
| *G02B 23/24* | (2006.01) |
| *G01K 15/00* | (2006.01) |
| *G01K 13/00* | (2006.01) |
| *G02B 23/26* | (2006.01) |

(Continued)

(52) U.S. Cl.
CPC ............ *A61B 1/127* (2013.01); *A61B 1/0008* (2013.01); *A61B 1/128* (2013.01); *G01K 3/005* (2013.01);

(Continued)

(58) Field of Classification Search
None
See application file for complete search history.

(56) References Cited

U.S. PATENT DOCUMENTS

2013/0030248 A1\*  1/2013 Matsumaru ........ A61B 1/00027
                                                                    600/110
2013/0116507 A1    5/2013 Segawa
(Continued)

FOREIGN PATENT DOCUMENTS

| CN | 103948364 A | 7/2014 |
| JP | 2013-254034 A | 12/2013 |

(Continued)

OTHER PUBLICATIONS

International Search Report dated Jul. 18, 2017 issued in PCT/JP2017/019358.

(Continued)

*Primary Examiner* — Timothy J Neal
(74) *Attorney, Agent, or Firm* — Scully, Scott, Murphy & Presser, P.C.

(57) ABSTRACT

An endoscope system includes: an endoscope having an insertion section adapted to be inserted into a subject; an optical member positioned at a distal end portion; a heating section configured to heat the optical member; a first temperature detector configured to detect first temperature information of the distal end portion; a second temperature detector connected in parallel with the heating section and configured to detect second temperature information of the distal end portion; a control unit configured to control the heating section based on the first temperature information; and an abnormality determination unit configured to determine presence or absence of abnormality in the first temperature detector and the second temperature detector based on the first temperature information and the second temperature information.

8 Claims, 9 Drawing Sheets

(51) Int. Cl.
*G01K 3/00* (2006.01)
*G01K 3/14* (2006.01)
*G01K 7/24* (2006.01)

(52) U.S. Cl.
CPC ............... *G01K 3/14* (2013.01); *G01K 7/24* (2013.01); *G01K 13/002* (2013.01); *G01K 15/007* (2013.01); *G02B 23/243* (2013.01); *G02B 23/2476* (2013.01); *G02B 23/2484* (2013.01); *G02B 23/26* (2013.01); *A61B 1/00096* (2013.01)

(56) References Cited

U.S. PATENT DOCUMENTS

2015/0080657 A1* 3/2015 Ide .................. A61B 1/127
600/117
2017/0172401 A1 6/2017 Ide et al.

FOREIGN PATENT DOCUMENTS

| JP | 2014-104037 A | 6/2014 |
| JP | 2014-150924 A | 8/2014 |
| JP | 2015-058149 A | 3/2015 |
| WO | WO 2012/039398 A1 | 3/2012 |
| WO | WO 2016/051516 A1 | 4/2016 |

OTHER PUBLICATIONS

Chinese Office Action dated Aug. 5, 2019 in Chinese Patent Application No. 201780003613.2.

* cited by examiner

ENDOSCOPE SYSTEM AND ENDOSCOPE

CROSS-REFERENCE TO RELATED APPLICATION

This application is a continuation of International Application No. PCT/JP2017/019358, filed on May 24, 2017, which claims the benefit of priority from Japanese Patent Application No. 2016-113496, filed on Jun. 7, 2016, the entire contents of which are incorporated herein by reference.

BACKGROUND

The present disclosure relates to an endoscope system and an endoscope.

In the related art, there is a known endoscope inserted into a subject for observation of a site to be examined. This type of endoscope is widely used in a medical field, or the like. An endoscope is used in a human body with high humidity and a temperature higher than room temperature, and when the distal end portion of an insertion section is inserted into the human body, this causes clouding on an optical member such as a lens cover and an objective lens arranged on the distal end portion, hindering acquisition of a clear image.

To solve this problem, there is proposed an endoscope apparatus including a heating member and a first temperature sensor arranged to come in contact with an objective lens, and including a second temperature sensor arranged on a side opposed to an illumination lens across the objective lens, and configured to control the heating member so as to allow the temperature detected by the first temperature sensor to be higher than the temperature detected by the second temperature sensor to prevent clouding of the objective lens (for example, refer to JP 2014-104037 A).

Moreover, there is a technique of connecting a heater and a thermistor with two or three wires to reduce diameter of an insertion section in a scanning type endoscope in order to eliminate image distortion due to temperature variation within a housing accommodating a light operating element such as an optical fiber (for example, refer to JP 2014-150924 A).

SUMMARY

An endoscope system according to one aspect of the present disclosure includes: an endoscope having an insertion section adapted to be inserted into a subject; an optical member positioned at a distal end portion; a heating section configured to heat the optical member; a first temperature detector configured to detect first temperature information of the distal end portion; a second temperature detector connected in parallel with the heating section and configured to detect second temperature information of the distal end portion; a control unit configured to control the heating section based on the first temperature information; and an abnormality determination unit configured to determine presence or absence of abnormality in the first temperature detector and the second temperature detector based on the first temperature information and the second temperature information.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
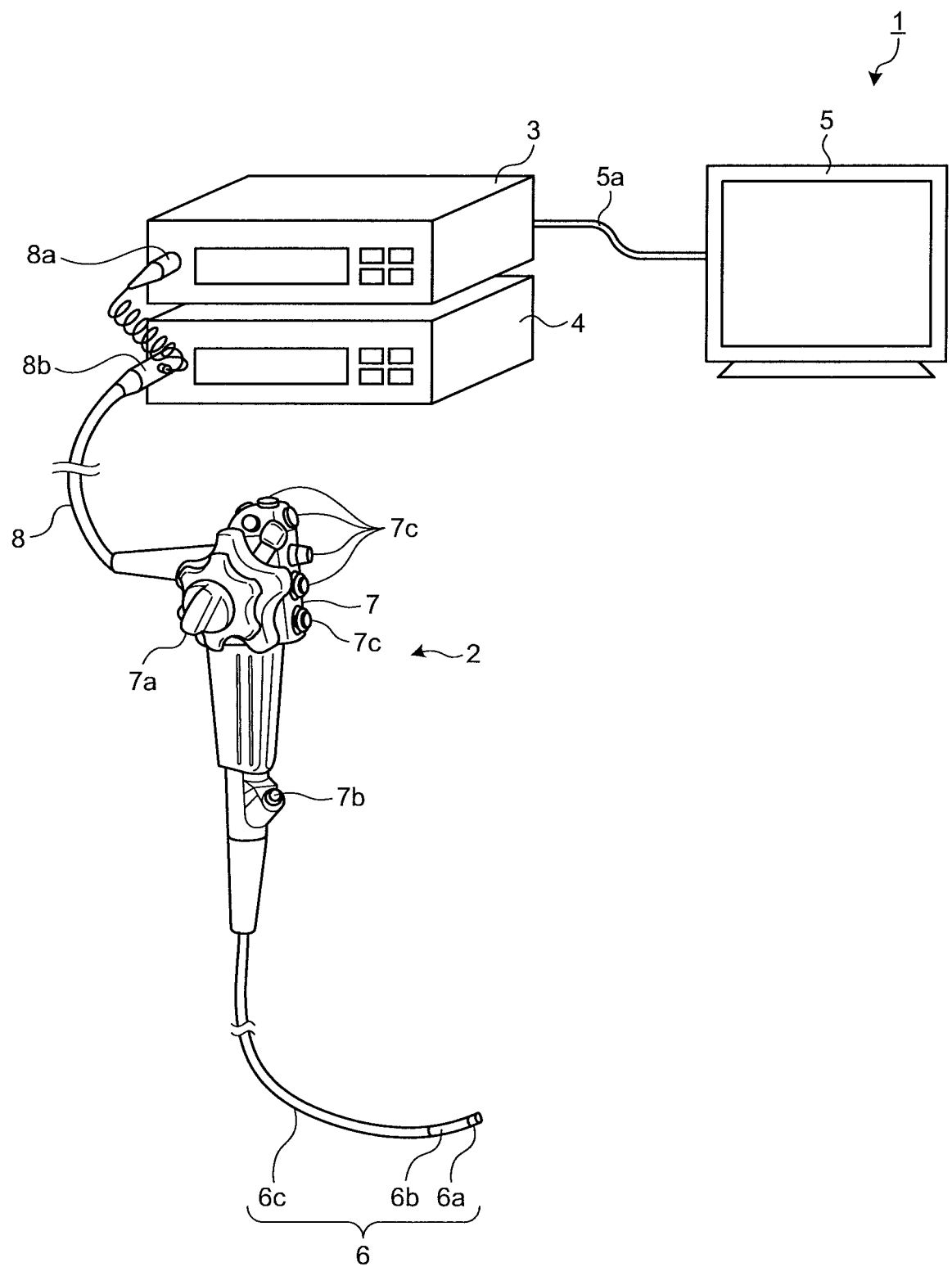
FIG. 1 is a block diagram schematically illustrating an overall configuration of an endoscope system according to an embodiment.

Hereinafter, an endoscope system will be described according to embodiments. Note that the present disclosure is not intended to be limited by these embodiments. In the drawings, same reference signs are attached to the same portions. Furthermore, it needs to be kept in mind that the drawings are schematic, and the relationship between the thickness and the width of individual members and the ratio between the members are different from an actual case. Still moreover, there are portions having different dimensions and ratios even between the drawings.

Embodiment

FIG. 1 is a block diagram schematically illustrating an overall configuration of an endoscope system according to an embodiment. As illustrated in FIG. 1, an endoscope system 1 according to the present embodiment includes an endoscope 2, an information processing apparatus 3, a light source apparatus 4, and a display device 5. The endoscope 2 is introduced into a subject and captures an image inside the body of a subject and generates an image signal of the interior of the subject. The information processing apparatus 3 performs predetermined image processing on the image signal captured by the endoscope 2 and controls each of portions of the endoscope system 1. The light source apparatus 4 generates illumination light for the endoscope 2. The display device 5 displays an image of the image signal after undergoing image processing by the information processing apparatus 3.

The endoscope 2 includes an insertion section 6, an operating unit 7, and a universal cord 8. The insertion section 6 is inserted into the subject. The operating unit 7 is arranged on a proximal end side of the insertion section 6 and gripped by an operator. The universal cord 8 has flexibility and extends from the operating unit 7.

The insertion section 6 is formed with an illumination fiber (light guide cable), an electric cable, an optical fiber, or the like. The insertion section 6 includes a distal end portion 6a, a bending portion 6b, and a flexible tube portion 6c. The distal end portion 6a includes an imaging unit described below. The bending portion 6b is a bendable portion formed with a plurality of bending pieces. The flexible tube portion 6c is flexible and provided on a proximal end side of the bending portion 6b. The distal end portion 6a includes an illumination unit, an observation unit, a forceps aperture 63, and an air/water feeding nozzle 62. The illumination unit illuminates an interior of the subject via an illumination lens. The observation unit captures the interior of the subject. The forceps aperture 63 communicates with a treatment instrument channel.

The operating unit 7 includes a bending knob 7a, a treatment instrument insertion section 7b, and a plurality of switching sections 7c. The bending knob 7a is used to bend the bending portion 6b in up-down and left-right directions. The treatment instrument insertion section 7b is a section through which a treatment instrument such as biological forceps and a laser knife is inserted into the body cavity of the subject. Each of the switching sections 7c is used to operate peripheral equipment such as the information processing apparatus 3, the light source apparatus 4, an air feeding apparatus, a water feeding apparatus, and a gas feeding apparatus. A treatment instrument inserted from the treatment instrument insertion section 7b passes through an internal treatment instrument channel and comes out from the forceps aperture 63 of the distal end of the insertion section 6.

The universal cord 8 includes an illumination fiber 12 and a cable. The universal cord 8 is branched at a proximal end. One end portion of the branched section is a connector 8a, and the other end portion is a connector 8b. The connector 8a is removably attached to the connector of the information processing apparatus 3. The connector 8b is removably attached to the light source apparatus 4. The universal cord 8 transmits illumination light emitted from the light source apparatus 4 to the distal end portion 6a via the connector 8b and the illumination fiber 12. Moreover, the universal cord 8 transmits an image signal captured by an imaging unit to be described below to the information processing apparatus 3 via the cable and the connector 8a.

The information processing apparatus 3 performs predetermined image processing on the image signal output from the connector 8a, while controlling the whole endoscope system 1. The information processing apparatus 3 controls a heating unit 10 (refer to FIG. 3) described below.

The light source apparatus 4 is configured with a light source that emits light, a condenser lens, or the like. Under the control of the information processing apparatus 3, the light source apparatus 4 emits light from the light source and supplies the light to the endoscope 2 connected via the connector 8b and the illumination fiber 12 of the universal cord 8, as illumination light supplied to the interior of the subject as an object.

The display device 5 includes a display using liquid crystal or organic electro luminescence (EL). The display device 5 displays, via a video cable 5a, various types of information including an image that has undergone predetermined image processing performed by the information processing apparatus 3. With this configuration, the operator may observe a desired position inside the subject and determine conditions by operating the endoscope 2 while viewing an image (in-vivo image) displayed by the display device 5.

Figure 2:
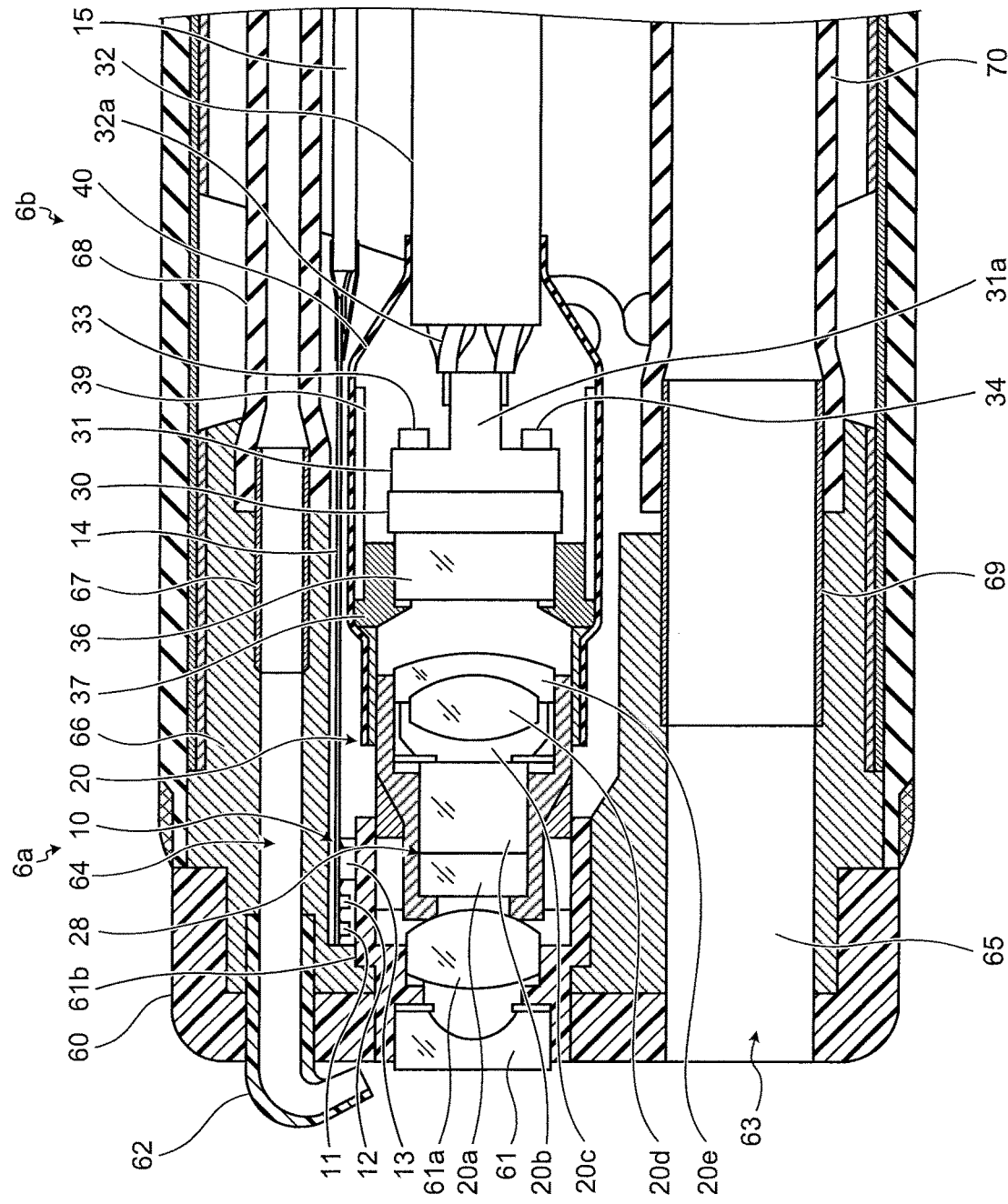
FIG. 2 is a cross-sectional view illustrating an internal configuration of a distal end portion of the endoscope illustrated in FIG. 1.

Next, a configuration of the distal end portion of the endoscope system 1 will be described. FIG. 2 is a cross-sectional view illustrating an internal configuration of the distal end portion 6a of the endoscope 2 illustrated in FIG. 1. As illustrated in FIG. 2, the distal end portion 6a positioned on the distal end side of the insertion section 6 of the endoscope system 1 is externally fitted by a distal end cover 60. The distal end cover 60 includes an observation window 61, an illumination lens (not illustrated), the air/water feeding nozzle 62, and the forceps aperture 63. An imaging apparatus 20 that images the inside of the subject is fittingly inserted in a holding section 61b of the observation window 61 via a plurality of lenses including a lens 61a. Behind the observation window 61, there is provided a distal end block 66 including an air/water feeding hole 64 and a forceps insertion hole 65 corresponding to the nozzle 62 and the forceps aperture 63, respectively.

At a rear end portion of the air/water feeding hole 64 on the distal end block 66, there is provided an air/water feeding pipe 67 to which an air/water feeding tube 68 is connected. At a rear end portion of the forceps insertion hole 65, there is provided a forceps insertion pipe 69 to which a forceps insertion tube 70 is connected.

The imaging apparatus 20 includes an objective optical unit 28 including a plurality of optical lenses 20a to 20e, an image sensor 30 arranged behind the objective optical unit 28 so as to receive light incident on the objective optical unit 28, a circuit substrate 31 connected to the image sensor 30, and a composite cable 32 connected to the image sensor 30 via the circuit substrate 31 so as to transmit an image signal of an image captured by the image sensor 30 to the information processing apparatus 3.

The light receiving surface side of the image sensor 30 includes a cover slip 36. An inner peripheral portion of an image sensor holding frame 37 is fitted to an outer peripheral portion of the cover slip 36 to be integrally fixed by an adhesive, or the like.

An IC 33 that processes an image signal received from the image sensor 30 into an electric signal and a chip capacitor 34 are mounted on a back surface of the circuit substrate 31. A cable 32a of the composite cable 32 is connected to a mounting portion 31a protruding on the back surface of the circuit substrate 31.

At a rear end portion of the image sensor holding frame 37, there is provided a shield frame 39 to cover the image sensor 30 and the circuit substrate 31. The outer peripheral portions of the shield frame 39 and the image sensor holding frame 37 are covered with a heat shrinkable tube 40.

Figure 3:
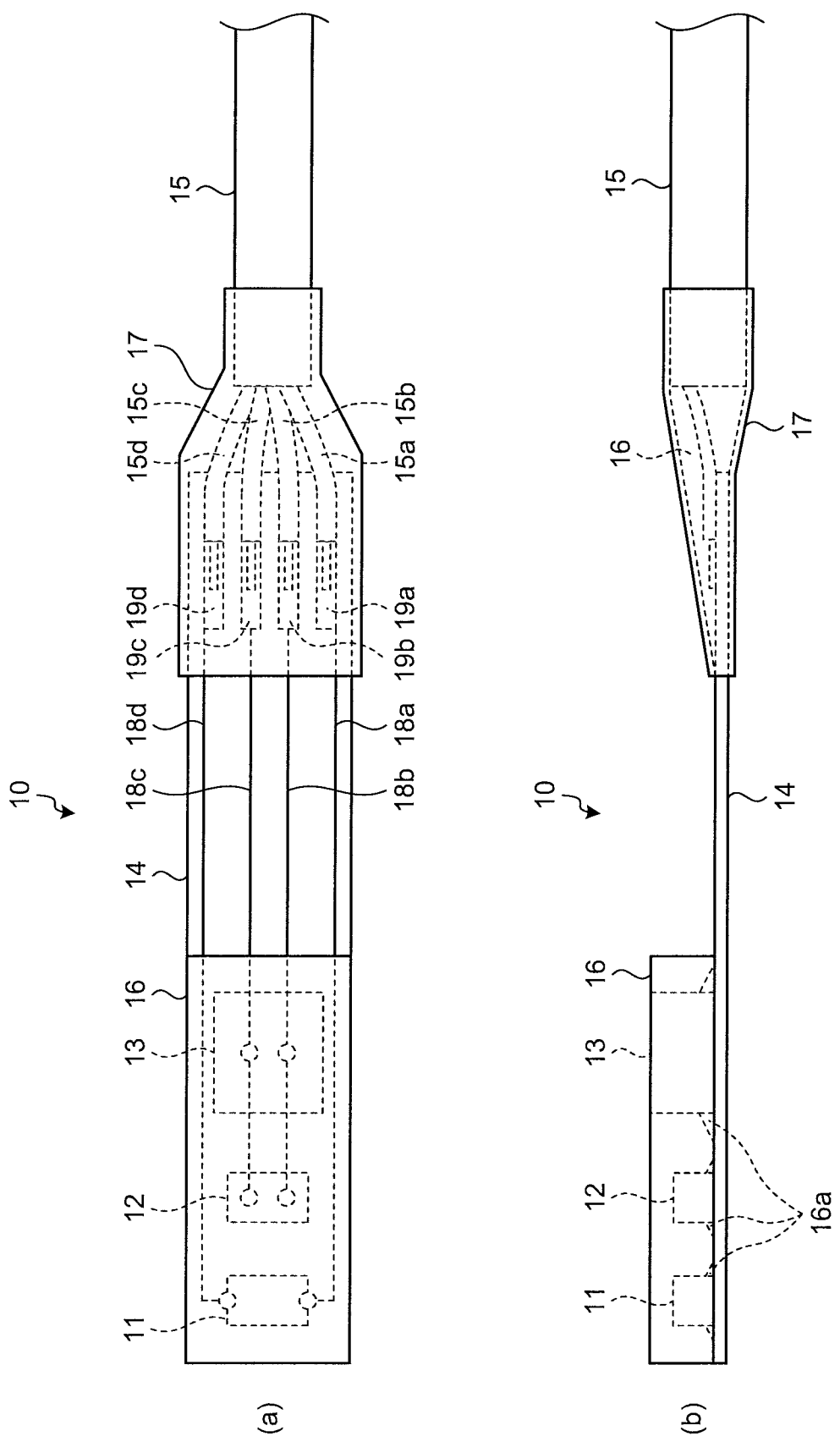
FIG. 3 is a top view and a side view of a heating unit used in FIG. 2.

The heating unit 10 is inserted between the holding section 61b into which the imaging apparatus 20 is fittingly inserted, and the distal end block 66. FIG. 3 includes a top view (FIG. 3(a)) and a side view (FIG. 3(b)) of the heating unit 10 used in FIG. 2.

The heating unit 10 includes a first temperature detector 11 to detect temperature information of the distal end portion 6a, a heating section (heater) 13 to heat optical members such as the observation window 61 and the lens 61a, and a second temperature detector 12 connected in parallel with the heating section 13 so as to detect temperature information of the distal end portion 6a. In the present embodiment, the first temperature detector 11, the second temperature detector 12, and the heating section 13 are arranged in a line in close proximity to each other in an optical axis direction. With arranging the first temperature detector 11, the second temperature detector 12, and the heating section 13 in a line in the optical axis direction, that is, linearly, it is possible to suppress the increase in the diameter of the distal end portion 6a. A thermistor is employed as the first temperature detector 11 and the second temperature detector 12.

The FPC substrate 14 has a length extending from the distal end portion 6a to the bending portion 6b and is arranged to set the distal end of the substrate to be positioned in the vicinity of the observation window 61, the lens 61a, and the optical members such as the optical lenses 20a to 20e. The first temperature detector 11, the second temperature detector 12, and the heating section 13 are mounted on the distal end side of the flexible printed circuit substrate 14 (hereinafter referred to as "FPC substrate 14"), that is, in the vicinity of the optical members, with regions surrounding a connecting portion being protected by an underfill agent 16a. The surface of the FPC substrate 14 on which the first temperature detector 11, the second temperature detector 12, and the heating section 13 are mounted is sealed with an encapsulating resin 16. The proximal end of the FPC substrate 14 extending to the bending portion 6b includes connection electrodes 19a to 19d to which cables 15a to 15d of a composite cable 15 are connected. The outer periphery of the proximal end connected with the cables 15a to 15d of the FPC substrate 14 is covered with a heat shrinkable tube 17, with the inside sealed with the encapsulating resin 16.

The first temperature detector 11 is a thermistor independent circuit connected to the cables 15a and 15d via wirings 18a and 18d and the connection electrodes 19a and 19d. The second temperature detector 12 and the heating section 13 are a heater-thermistor parallel circuit connected to the cables 15b and 15c via the wiring 18b and 18c and the connection electrodes 19b and 19c. In the present embodiment, the temperature of the distal end portion 6a is mainly detected by the thermistor independent circuit including the first temperature detector 11, and the thermistor-heater parallel circuit including the second temperature detector 12 and the heating section 13 detects the temperature of the distal end portion 6a to detect abnormality of the first temperature detector 11 and/or the second temperature detector 12 while performing temperature control of the distal end portion 6a.

The heating unit 10 sets the heating section 13 with an upper surface being exposed from the encapsulating resin 16, to be brought into contact with the holding section 61b to be fixed. An end portion on the proximal end side (side to which the composite cable 15 is connected) of the FPC substrate 14 is prepared to have a length to be positioned in the vicinity of a boundary between the distal end portion 6a and the bending portion 6b.

Figure 4:
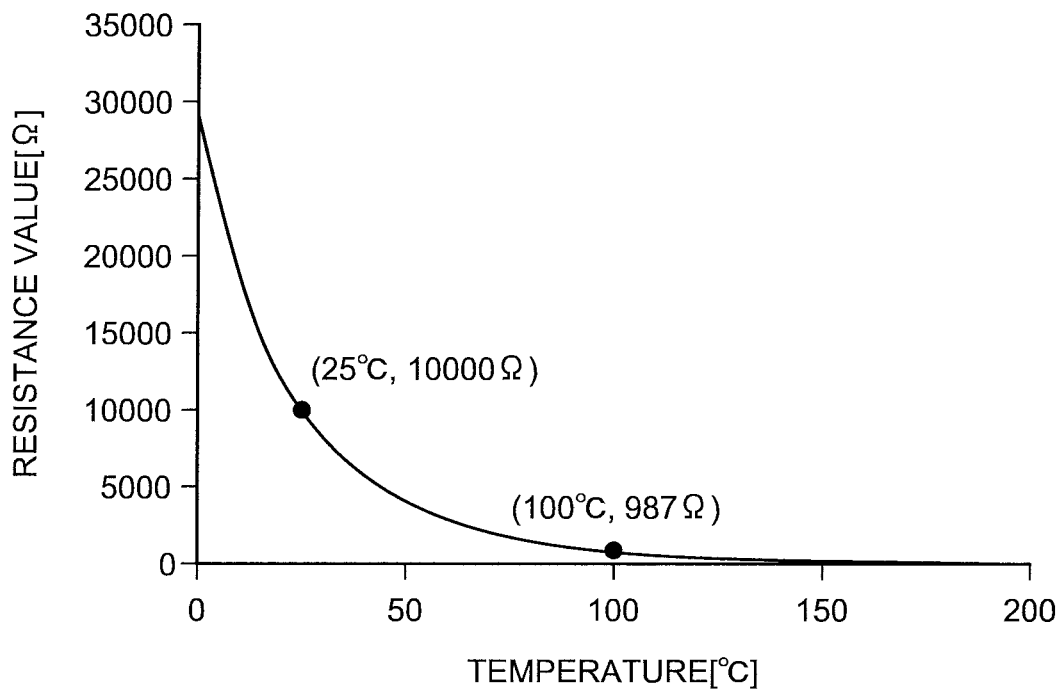
FIG. 4 is a graph illustrating a temperature resistance characteristic of a thermistor used as a first temperature detector and a second temperature detector.

With the use of a negative temperature coefficient (NTC) thermistor (B constant: 3435, reference resistance: 10 KΩ (25° C.)) having a temperature resistance characteristic illustrated in FIG. 4 as the first temperature detector 11, for example, the resistance of the thermistor decreases with an increase of the temperature of the distal end portion 6a because of this temperature resistance characteristic. Accordingly, by obtaining the resistance value of the thermistor circuit including the first temperature detector 11, it is possible to detect the temperature of the distal end portion 6a with high accuracy.

Figure 5:
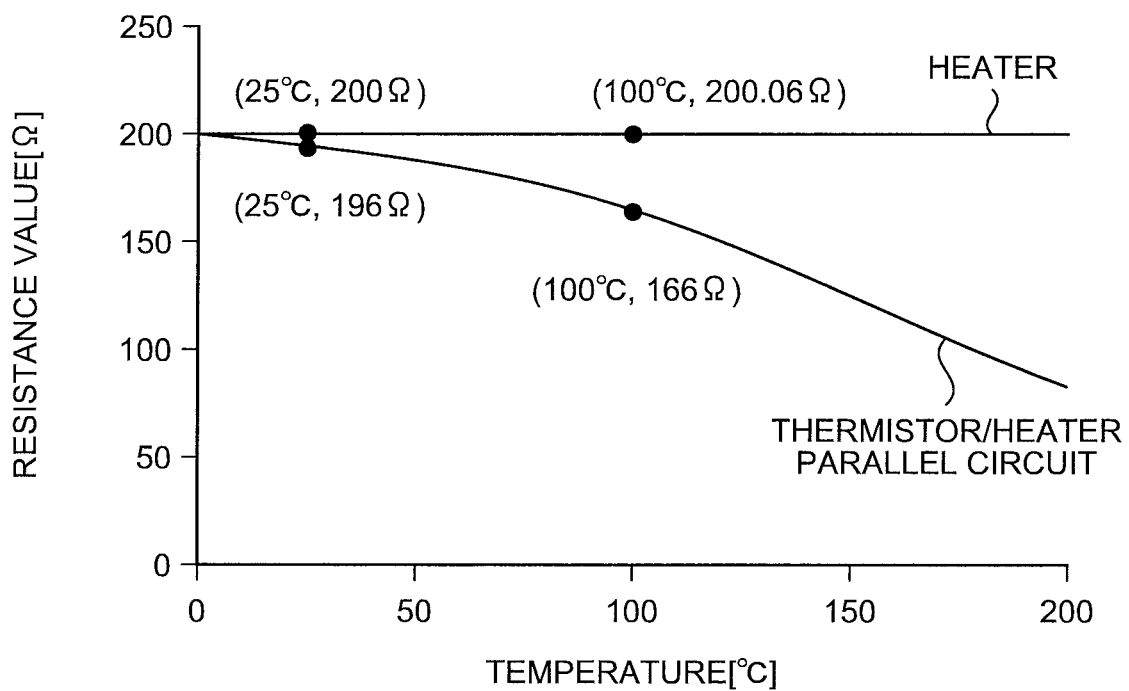
FIG. 5 is a graph illustrating a temperature resistance characteristic of a heater/thermistor series circuit in a case where the thermistor of FIG. 4 is used as the second temperature detector.

With the use of a thermistor having a temperature resistance characteristic illustrated in FIG. 4 having a specification similar to that of the first temperature detector 11, as the second temperature detector 12, and with the use of a heater having a temperature resistance characteristic (temperature coefficient: 100 ppm/° C., reference resistance: 200Ω (25° C.)) illustrated in FIG. 5 as the heating section 13, for example, it is possible to detect the temperature of the distal end portion 6a by obtaining the resistance value of the heater/thermistor parallel circuit because the resistance of the thermistor has very high temperature dependence while the resistance of the heater independent circuit has very low temperature dependence, as illustrated in FIG. 5. Note that the first temperature detector 11 is not limited to the NTC thermistor and it is possible to use a positive temperature coefficient (PTC) thermistor or the like. Still, it is preferable to use the NTC thermistor as the second temperature detector 12.

It is possible to calculate a resistance value Rp of the heater/thermistor parallel circuit using a heater resistance Rh and a thermistor resistance Rt by the following equation.

$$Rp=1/(1/Rh+1/Rt)$$

Note that FIGS. 4 and 5 are illustrative and there is no need to use the same type of thermistor as the first temperature detector 11 and the second temperature detector 12.

Figure 6:
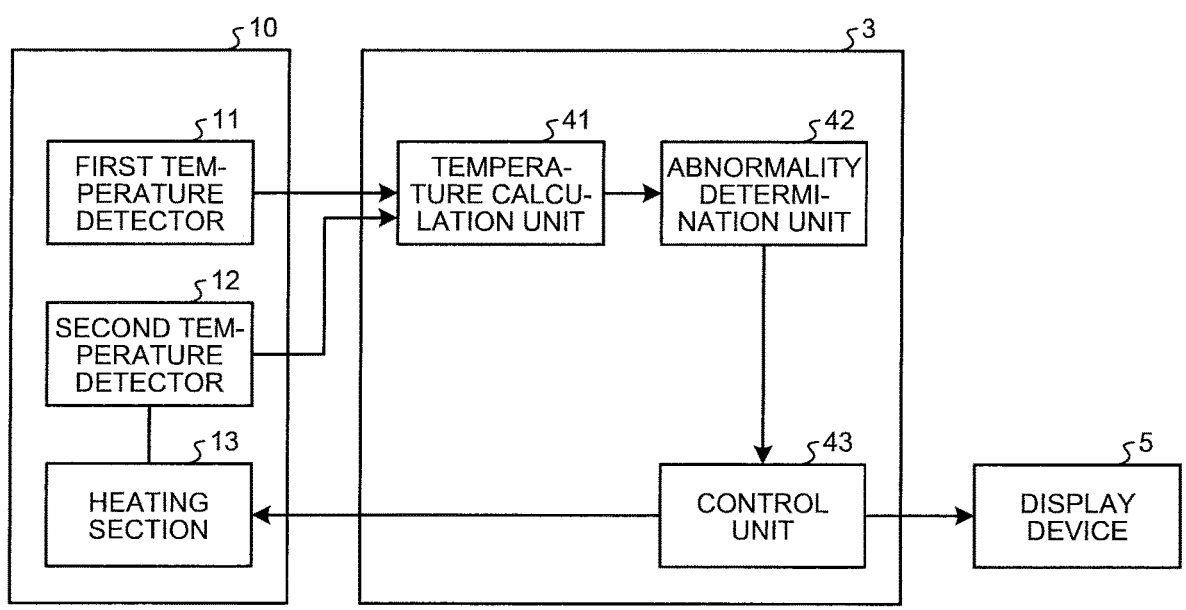
FIG. 6 is a block diagram of a system including the heating unit illustrated in FIG. 3.

FIG. 6 is a block diagram of a system including the heating unit 10 illustrated in FIG. 3. As illustrated in FIG. 6, the information processing apparatus 3 includes a temperature calculation unit 41, an abnormality determination unit 42, and a control unit 43. The temperature calculation unit 41 calculates the temperature of the distal end portion 6a. The abnormality determination unit 42 determines abnormality in the first temperature detector 11 and the second temperature detector 12 based on the temperature of the distal end portion 6a calculated by the temperature calculation unit 41. The control unit 43 controls the heating section 13 based on the temperature of the distal end portion 6a calculated by the temperature calculation unit 41.

Based on the resistance value output from the thermistor circuit including the first temperature detector 11, the temperature calculation unit 41 calculates a temperature T1 (first distal end portion temperature) of the distal end portion 6a. In addition, based on the resistance value output from the heater/thermistor circuit including the second temperature detector 12 and the heating section 13, the temperature calculation unit 41 calculates a temperature T2 (second distal end portion temperature) of the distal end portion 6a.

The abnormality determination unit 42 determines abnormality of the first temperature detector 11 based on the temperature T1 of the distal end portion 6a calculated by the temperature calculation unit 41 from the resistance value output from the thermistor circuit including the first temperature detector 11. The abnormality determination unit 42 further determines abnormality of the second temperature detector 12 based on the temperature T2 of the distal end portion 6a calculated by the temperature calculation unit 41 from the resistance value output from the heater/thermistor circuit including the second temperature detector 12 and the heating section 13. Furthermore, the abnormality determination unit 42 determines abnormality of the first temperature detector 11 or the second temperature detector 12 based on a difference between the temperature T1 and the temperature T2. In a case where abnormality is found in the first temperature detector 11 and/or the second temperature detector 12, the abnormality determination unit 42 outputs the information to the control unit 43.

The control unit 43 controls the heating section 13 to set the temperature T1 of the distal end portion 6a calculated by the temperature calculation unit 41 to a target temperature T0 of the distal end portion 6a based on the resistance value output from the thermistor circuit including the first temperature detector 11. In a case where the abnormality determination unit 42 determines that the first temperature detector 11 or the second temperature detector 12 is abnormal, the control unit 43 stops power supply to the heating section 13 and outputs the abnormality of the first temperature detector 11 on the display device 5.

Figure 7:
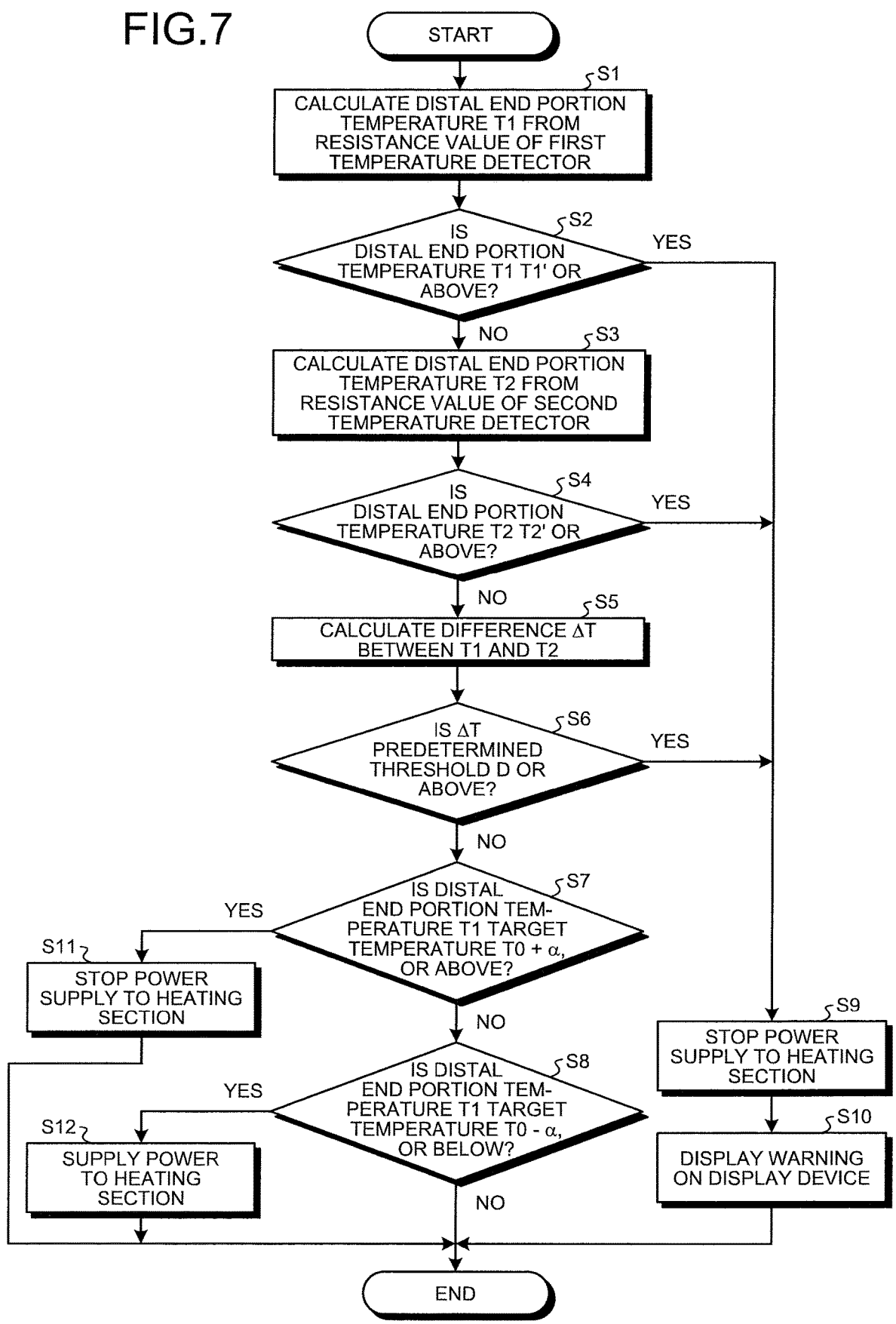
FIG. 7 is a flowchart illustrating the temperature control of the distal end portion according to an embodiment.

Next, temperature control of the distal end portion 6a according to the present embodiment will be described with reference to the drawings. FIG. 7 is a flowchart illustrating the temperature control of the distal end portion 6a according to the embodiment.

First, the temperature calculation unit 41 calculates the temperature T1 of the distal end portion 6a from the resistance value of the thermistor circuit including the first temperature detector 11 (Step S1).

The abnormality determination unit 42 determines whether the temperature T1 of the distal end portion 6a calculated by the temperature calculation unit 41 is a set temperature T1' or above (Step S2). The set temperature T1' is a temperature by which the first temperature detector 11 may determine that the temperature is abnormally higher than the target temperature T0. The set temperature T1' is a temperature obtained by adding variation of temperature detection calculated from the thermistor circuit including the first temperature detector 11 to a maximum allowable temperature of the distal end portion 6a.

In a case where the abnormality determination unit 42 determines that the temperature T1 of the distal end portion 6a is the set temperature T1' or above (Step S2: Yes), the control unit 43 stops power supply to the heater/thermistor parallel circuit including the heating section 13 (Step S9) and displays a warning on the display device 5 (Step S10).

In contrast, in a case where the abnormality determination unit 42 determines that the temperature T1 of the distal end portion 6a is below the set temperature T1' (Step S2: No), the temperature calculation unit 41 calculates the temperature T2 of the distal end portion 6a from the resistance value of the heater/thermistor circuit including the second temperature detector 12 and the heating section 13 (Step S3).

The abnormality determination unit 42 determines whether the temperature T2 of the distal end portion 6a calculated by the temperature calculation unit 41 is a set temperature T2' or above (Step S4). The set temperature T2' is a temperature by which the second temperature detector 12 may judge that the temperature is abnormally higher than the target temperature T0. The set temperature T2' is a temperature obtained by adding variation of temperature detection calculated from the heater/thermistor circuit including the second temperature detector 12 to a maximum allowable temperature of the distal end portion 6a. The variation in temperature detection is higher in the heater/thermistor circuit than in the thermistor independent circuit, resulting in T2' higher than T1'.

In a case where the abnormality determination unit 42 determines that the temperature T2 of the distal end portion 6a is the set temperature T2' or above (Step S4: Yes), the control unit 43 stops power supply to the heater/thermistor parallel circuit including the heating section 13 (Step S9) and displays a warning on the display device 5 (Step S10).

In contrast, in a case where the abnormality determination unit 42 determines that the temperature T2 of the distal end portion 6a is below the set temperature T2' (Step S4: No), the temperature calculation unit 41 calculates a difference $\Delta T$ between T1 and T2 (Step S5).

The abnormality determination unit 42 determines whether $\Delta T$ calculated by the temperature calculation unit 41 is a predetermined threshold D or above (Step S6). The threshold D is a value used to determine that any of the first temperature detector 11 and the second temperature detector 12 is faulty and is a value obtained by adding variation of temperature detection in each of the circuits to a maximum temperature difference between the first temperature detector 11 and the second temperature detector 12.

In a case where the abnormality determination unit 42 determines that $\Delta T$ is the threshold D or above (Step S6: Yes), the control unit 43 stops power supply to the heater/thermistor parallel circuit including the heating section 13 (Step S9) and displays a warning on the display device (Step S10).

In contrast, in a case where the abnormality determination unit 42 determines that AT is below the threshold D (Step S6: No), the abnormality determination unit 42 further determines whether the temperature T1 of the distal end portion 6a is the target temperature T0+α, or above (Step S7). α may be set from the behavior of the detected temperature of the first temperature detector 11.

In a case where the abnormality determination unit 42 determines that the temperature T1 is the target temperature T0+α, or above (Step S7: Yes), the control unit 43 stops power supply to the heater/thermistor parallel circuit including the heating section 13 (Step S11).

In contrast, in a case where the abnormality determination unit 42 determines that the temperature T1 is below the target temperature T0+α (Step S7: No), the abnormality determination unit 42 further determines whether the temperature T1 of the distal end portion 6a is the target temperature T0−α, or below (Step S8).

In a case where the abnormality determination unit 42 determines that the temperature T1 is the target temperature T0−α, or below (Step S8: Yes), the control unit 43 supplies power to the heater/thermistor parallel circuit including the heating section 13 until the temperature reaches the target temperature T0 (Step S12).

In a case where the abnormality determination unit 42 determines that the temperature T1 is above the target temperature T0−α (Step S8: No), the processing is finished.

The present embodiment connects the second temperature detector 12 in parallel with the heating section 13 to enable detection of the temperature of the distal end portion 6a from the thermistor independent circuit including the first temperature detector 11 and the heater/thermistor parallel circuit without increasing the number of wires and connectors. With this configuration, it is possible to detect the temperature of the distal end portion 6a with higher precision and control the temperature of the distal end portion 6a with high accuracy while reducing the diameter of the distal end portion 6a.

While the above-described embodiment is a case where the temperature calculation unit 41 calculates the temperature T2 of the distal end portion 6a based on the resistance value output from the heater/thermistor circuit including the second temperature detector 12 and the heating section 13, it is preferable to calculate the temperature T2 based on the resistance value obtained by subtracting the resistance Rc of the cables 15b and 15c from the resistance value of the heater/thermistor parallel circuit to which the heating section 13 and the second temperature detector 12 are connected, in order to detect the temperature with higher precision.

A resistance Rc of the connected cables 15b and 15c is high relative to the resistance value Rp of the heater/thermistor parallel circuit in the heater/thermistor parallel circuit. Accordingly, the temperature of the distal end portion 6a is calculated using a resistance Rp' (Rp'=Rp−Rc) obtained by subtracting the cable resistance Rc, as the resistance value of the heater/thermistor parallel circuit, making it possible to calculate a temperature T2 of the distal end portion 6a with higher precision.

Figure 8:
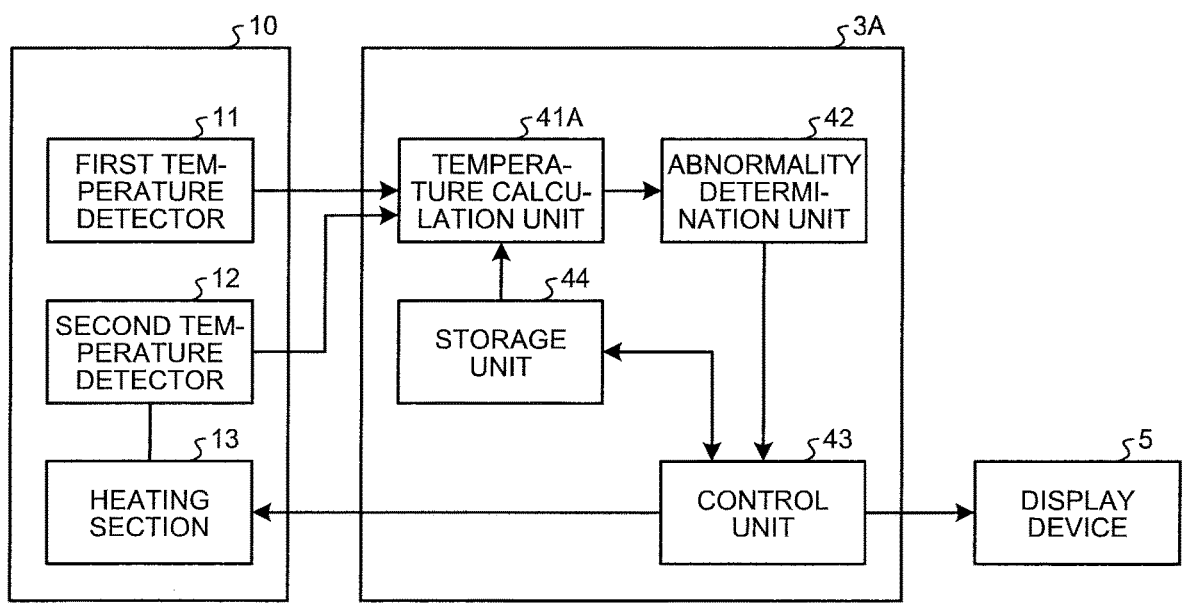
FIG. 8 is a block diagram of a system including a heating unit according to a first modification of the embodiment.

FIG. 8 is a block diagram of a system including the heating unit 10 according to a first modification of the embodiment. An information processing apparatus 3A includes a storage unit 44 that stores the resistances Rc of the cables 15b and 15c connected to the heating section 13 and the second temperature detector 12. A temperature calculation unit 41A calculates the temperature T2 of the distal end portion 6a based on a value obtained by subtracting the cable resistance Rc from the resistance value Rp of the heater/thermistor parallel circuit to which the heating section 13 and the second temperature detector 12 are connected.

Figure 9:
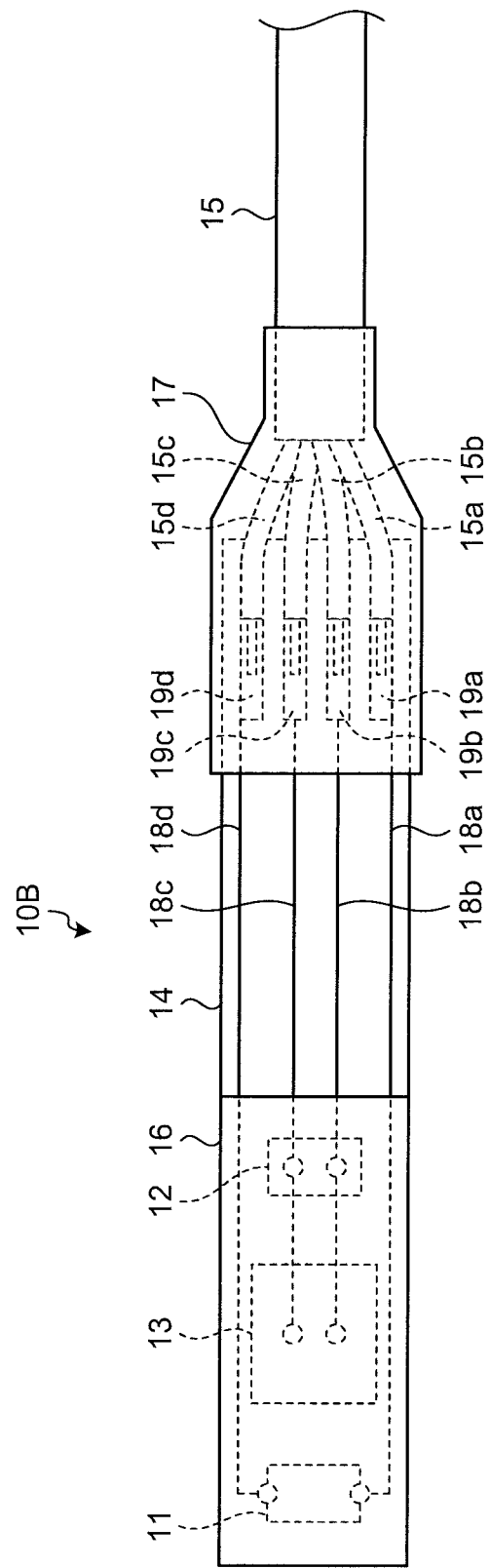
FIG. 9 is a top view of a heating unit according to a second modification of the embodiment.
Figure 10:
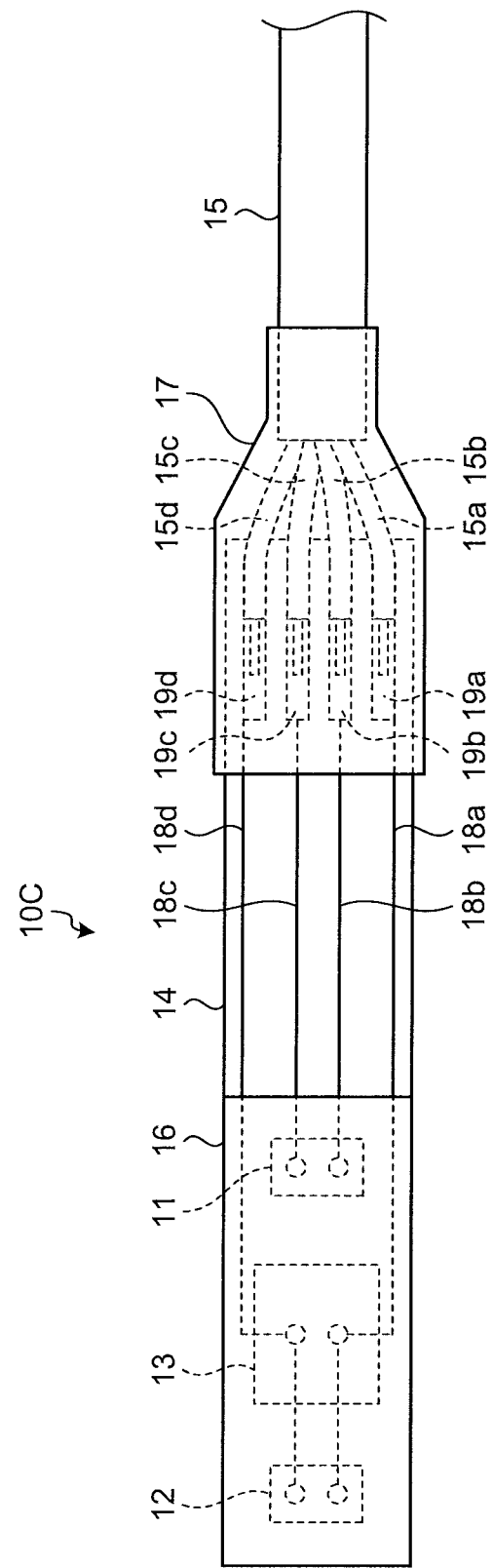
FIG. 10 is a top view of a heating unit according to a third modification of the embodiment.

Moreover, it is satisfactory that the heating unit 10 arranges the first temperature detector 11, the second temperature detector 12, and the heating section 13 in a line, that is, linearly, in the optical axis direction, and the arrangement order is not limited to the above-described example of the embodiment. FIGS. 9 and 10 are top views of a heating unit according to second and third modifications of the embodiment.

In a heating unit 10B of the second modification illustrated in FIG. 9, the first temperature detector 11, the heating section 13, and the second temperature detector 12 are arranged in this order from the distal end side. In a heating unit 100 of the third modification illustrated in FIG. 10, the second temperature detector 12, the heating section 13, and the first temperature detector 11 are arranged in this order from the distal end side. On the conditions that the first temperature detector 11, the second temperature detector 12, and the heating section 13 are arranged in a line in the optical axis direction, the second temperature detector 12 and the heating section 13 form a parallel circuit, and the length of the heating unit in a direction orthogonal to the optical axis direction is suppressed from being enlarged due to wiring, it is possible to perform precise temperature control of the distal end portion 6a and to achieve the distal end portion 6a having a small diameter.

While the above embodiment is an exemplary case of a flexible endoscope in which the insertion section 6 includes the distal end portion 6a, the bending portion 6b, and the flexible tube portion 6c, the present disclosure is not limited to this and applicable to a rigid endoscope in a similar manner.

The endoscope is useful for an endoscope system needing an image of high image quality and reduction of the diameter of the distal end portion.

According to the present disclosure, it is possible to control the temperature of the distal end portion of the endoscope with high accuracy while suppressing the increase in the diameter of the distal end portion.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
    an endoscope having an insertion section configured to be inserted into a subject;
    an optical member positioned at a distal end of the insertion section;
    a heater configured to heat the optical member;
    a first temperature sensor configured to detect first temperature information of the distal end portion;
    a second temperature sensor connected in parallel with the heater and configured to detect second temperature information of the distal end portion;
    a processor comprising hardware, the processor being configured to:
        control the heater based on the first temperature information; and
        determine presence or absence of abnormality in the first temperature sensor and the second temperature sensor based on the first temperature information and the second temperature information.

2. The endoscope system according to claim 1, wherein the second temperature sensor is an NTC thermistor.

3. The endoscope system according to claim 1, wherein the processor is further configured to:
    store a cable resistance of a cable connected to the heater and the second temperature sensor; and
    calculate a first distal end portion temperature from a resistance value of a circuit to which the first temperature sensor is connected and calculate a second distal end portion temperature based on a value obtained by subtracting the cable resistance from a resistance value of a parallel circuit to which the heater and the second temperature sensor are connected,
    wherein the processor is configured to determine presence or absence of abnormality in the heater, the first temperature sensor, and the second temperature sensor based on the first distal end portion temperature and the second distal end portion temperature.

4. The endoscope system according to claim 1, wherein the processor is configured to determine presence or absence of abnormality in the heater, the first temperature sensor, and the second temperature sensor based on a difference between the first distal end portion temperature and the second distal end portion temperature.

5. The endoscope system according to claim 1, wherein the second temperature sensor and the heater are arranged in a line in a direction of a longitudinal axis of the insertion section.

6. An endoscope comprising:
    an insertion section configured to be inserted into a subject;
    an optical member positioned at a distal end of the insertion section;
    a heater configured to heat the optical member;
    a first temperature sensor configured to detect first temperature information of the distal end portion; and
    a second temperature sensor connected in parallel with the heater and configured to detect second temperature information of the distal end portion,
    wherein the heater, the first temperature sensor, and the second temperature sensor are arranged in vicinity of the optical member.

7. The endoscope according to claim 6, wherein the second temperature sensor is an NTC thermistor.

8. The endoscope according to claim 6, further comprising:
    a flexible printed circuit substrate with a distal end being positioned in the vicinity of the optical member; and
    a plurality of cables connected to a proximal end of the flexible printed circuit substrate,
    wherein the heater, the first temperature sensor, and the second temperature sensor are mounted on a distal end of the flexible printed circuit substrate and are electrically connected to the cables.

* * * * *